United States Patent
Siegel

(10) Patent No.: US 8,167,860 B1
(45) Date of Patent: May 1, 2012

(54) PANTY LINER/PAD SYSTEM

(76) Inventor: Linda Siegel, Sarasota, FL (US)

(*) Notice: Subject to any disclaimer, the term of this patent is extended or adjusted under 35 U.S.C. 154(b) by 272 days.

(21) Appl. No.: 12/456,957

(22) Filed: Jun. 25, 2009

Related U.S. Application Data

(60) Provisional application No. 61/088,421, filed on Aug. 13, 2008.

(51) Int. Cl.
*A61F 13/15* (2006.01)
(52) U.S. Cl. .......... 604/385.04; 604/385.01; 604/385.17
(58) Field of Classification Search ............ 604/385.17, 604/385.04, 385.01
See application file for complete search history.

(56) References Cited

U.S. PATENT DOCUMENTS

| 6,398,770 | B1 * | 6/2002 | Drevik ..................... 604/385.01 |
| 6,932,801 | B1 * | 8/2005 | Samuelsson ............. 604/385.17 |
| 7,530,973 | B2 * | 5/2009 | Tanio et al. ............... 604/385.27 |
| 2002/0065497 | A1 * | 5/2002 | Kolby-Falk ................ 604/368 |
| 2002/0165512 | A1 * | 11/2002 | Drevik et al. ................ 604/380 |
| 2005/0267433 | A1 * | 12/2005 | Tanio et al. ............... 604/385.17 |
| 2006/0135934 | A1 * | 6/2006 | Gilbert ..................... 604/385.101 |
| 2006/0142725 | A1 * | 6/2006 | Fujikawa et al. ......... 604/385.04 |

* cited by examiner

*Primary Examiner* — Lynne Anderson
*Assistant Examiner* — Bradley Philips

(57) ABSTRACT

A body portion has opposed ends spaced centrally by a length. The body portion has opposed concave sides. The concave sides are spaced by a minimum width when measured at the midpoint of the length. The body portion has planar upper and lower surfaces. A vertically oriented projection extends upwardly from the upper surface of the body portion. The body portion has a lower edge centrally positioned on the longitudinal axis of the body portion. The projection has an upper edge centrally positioned above the longitudinal axis of the body portion. The projection has a forward end in a generally triangular configuration. The projection has a rearward end in a generally triangular configuration. The forward end has a thickness greater than the thickness of the rearward end.

1 Claim, 3 Drawing Sheets

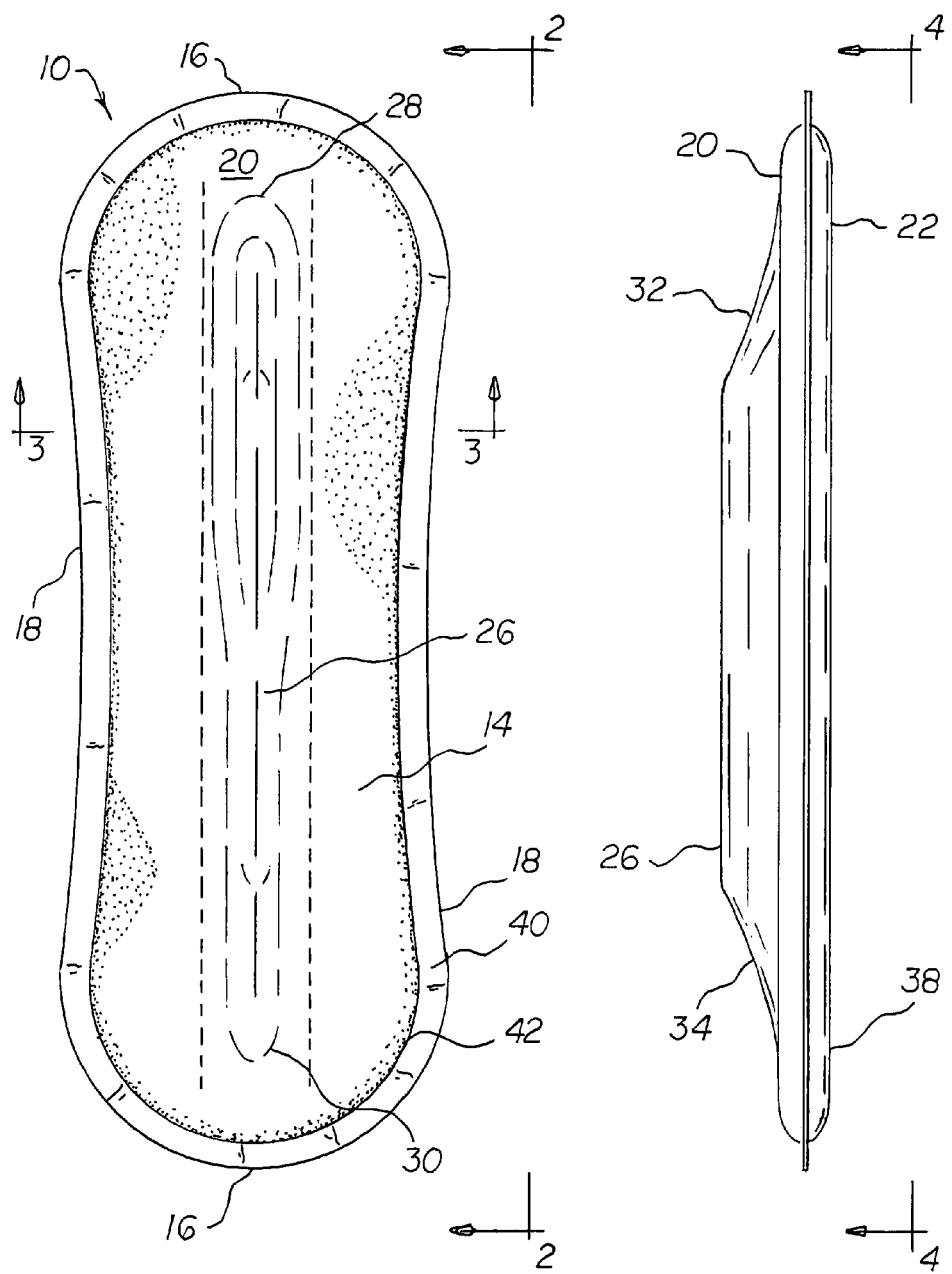

PANTY LINER/PAD SYSTEM

RELATED APPLICATION

The present non-provisional patent application is based upon Provisional Patent Application No. 61/088,421 filed Aug. 13, 2008, the subject matter of which is incorporated herein by reference.

BACKGROUND OF THE INVENTION

1. Field of the Invention

The present invention relates to a panty liner/pad system and more particularly pertains to securing panty liners and menstrual pads in a proper absorbing position through an interlabial projection, the securing being effected in a comfortable, reliable, hygienic, sanitary, convenient and economical manner.

2. Description of the Prior Art

The use of sanitary pads of known designs and configurations is known in the prior art. More specifically, sanitary pads of known designs and configurations previously devised and utilized for the purpose of securing sanitary pads through known methods and apparatuses are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 7,217,259 issued May 15, 2007 to McDaniel relates to an Interlabial Absorbent Article. U.S. Pat. No. 5,702,380 issued Dec. 30, 1997 to Walker relates to a Sanitary Napkin. Lastly, U.S. Pat. No. 5,672,165 issued Sep. 30, 1997 to Belecky relates to a Menstrual Hygiene Product.

While these devices fulfill their respective, particular objectives and requirements, the aforementioned patents do not describe a panty liner/pad system that allows for securing panty liners and menstrual pads in a proper absorbing position through an interlabial projection, the securing being effected in a comfortable, reliable, hygienic, sanitary, convenient and economical manner.

In this respect, the panty liner/pad system according to the present invention substantially departs from the conventional concepts and designs of the prior art, and in doing so provides an apparatus primarily developed for the purpose of securing panty liners and menstrual pads in a proper absorbing position through an interlabial projection, the securing being effected in a comfortable, reliable, hygienic, sanitary, convenient and economical manner.

Therefore, it can be appreciated that there exists a continuing need for a new and improved panty liner/pad system which can be used for securing panty liners and menstrual pads in a proper absorbing position through an interlabial projection, the securing being effected in a comfortable, reliable, hygienic, sanitary, convenient and economical manner. In this regard, the present invention substantially fulfills this need.

SUMMARY OF THE INVENTION

In view of the foregoing disadvantages inherent in the known types of sanitary pads of known designs and configurations now present in the prior art, the present invention provides an improved panty liner/pad system. As such, the general purpose of the present invention, which will be described subsequently in greater detail, is to provide a new and improved panty liner/pad system and method which has all the advantages of the prior art and none of the disadvantages.

To attain this, the present invention essentially comprises a panty liner/pad system. First provided is a body portion. The body portion has opposed semicircular ends. The ends are spaced centrally by a length of between 6.25 and 7.0 inches. The body portion has opposed concave sides. The concave sides are spaced centrally by a maximum width of between 2.15 and 2.35 inches when measured at the midpoint of the length. The concave sides are spaced by a minimum width of between 2.4 and 2.6 inches when measured adjacent to the ends. The body portion has a longitudinal axis. In this manner the body portion is divided into two symmetrically shaped lateral halves. The body portion has a latitudinal axis. In this manner the body portion is divided into two symmetrically shaped longitudinal halves. The body portion prior to use has a planar upper surface. The body portion prior to use also has a planar lower surface. The upper and lower planar surfaces are spaced by a thickness of between 0.5 and 1.0 inch over the majority of their extents.

A vertically oriented projection is provided. The projection extends upwardly from the upper surface of the body portion. The projection is integrally formed with the body portion. The body portion has a lower edge. The lower edge is centrally positioned on the longitudinal axis of the body portion. The lower edge has a length of between 4.0 and 5.0 inches. The projection has an upper edge. The upper edge is centrally positioned above the longitudinal axis of the body portion. The upper edge has a length of between 0.7 and 0.8 inches. The projection has a forward end. The forward end is in a generally triangular configuration. The projection has a rearward end. The rearward end is in a generally triangular configuration. The forward and rearward ends each have a concave edge. The concave edge is provided between the upper and lower edges of the projection. The forward end and the projection there adjacent have a thickness between 25 and 50 percent greater than the thickness of the rearward end and projection there adjacent. The body portion and the projection are adapted to curve with the user's vagina and are held in place by the user's labia majora during use.

Further provided is a sheet of a moisture impervious material. The sheet has a periphery. The periphery has stitching. In this manner the sheet is attached to the lower surface of the body portion adjacent to the periphery. The sheet is fabricated of a moisture impervious material. The body portion and the projection are fabricated of a moisture absorbing material.

Provided next is a pair of adhesive strips. The strips are coupled to the lower surface of the body portion. The strips are positioned parallel with and laterally spaced from the longitudinal centerline. The strips are adapted to removably couple the body portion to panties of the user concurrently with the projection being held by the labia majora of the user.

Provided last are two parallel lines of stitching through the body portion on opposite sides of the projection.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved panty liner/pad system which has all of the advantages of the prior art sanitary pads of known designs and configurations and none of the disadvantages.

It is another object of the present invention to provide a new and improved panty liner/pad system which may be easily and efficiently manufactured and marketed.

It is further object of the present invention to provide a new and improved panty liner/pad system which is of durable and reliable constructions.

An even further object of the present invention is to provide a new and improved panty liner/pad system which is susceptible of a low cost of manufacture with regard to both materials and labor, and which accordingly is then susceptible of low prices of sale to the consuming public, thereby making such panty liner/pad system economically available to the buying public.

Even still another object of the present invention is to provide a panty liner/pad system for securing panty liners and menstrual pads in a proper absorbing position through an interlabial projection, the securing being effected in a comfortable, reliable, hygienic, sanitary, convenient and economical manner.

Lastly, it is an object of the present invention to provide a new and improved panty liner/pad system. A body portion has opposed ends spaced centrally by a length. The body portion has opposed concave sides. The concave sides are spaced by a minimum width when measured at the midpoint of the length. The body portion has planar upper and lower surfaces. A vertically oriented projection extends upwardly from the upper surface of the body portion. The body portion has a lower edge centrally positioned on the longitudinal axis of the body portion. The projection has an upper edge centrally positioned above the longitudinal axis of the body portion. The projection has a forward end in a generally triangular configuration. The projection has a rearward end in a generally triangular configuration. The forward end has a thickness greater than the thickness of the rearward end.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a plan view of a panty liner/pad system constructed in accordance with the principles of the present invention.

FIG. 2 is a side elevational view of the panty liner/pad taken along line 2-2 of FIG. 1.

The same reference numerals refer to the same parts throughout the various Figures.

DESCRIPTION OF THE PREFERRED EMBODIMENT

Figures 3, 4:
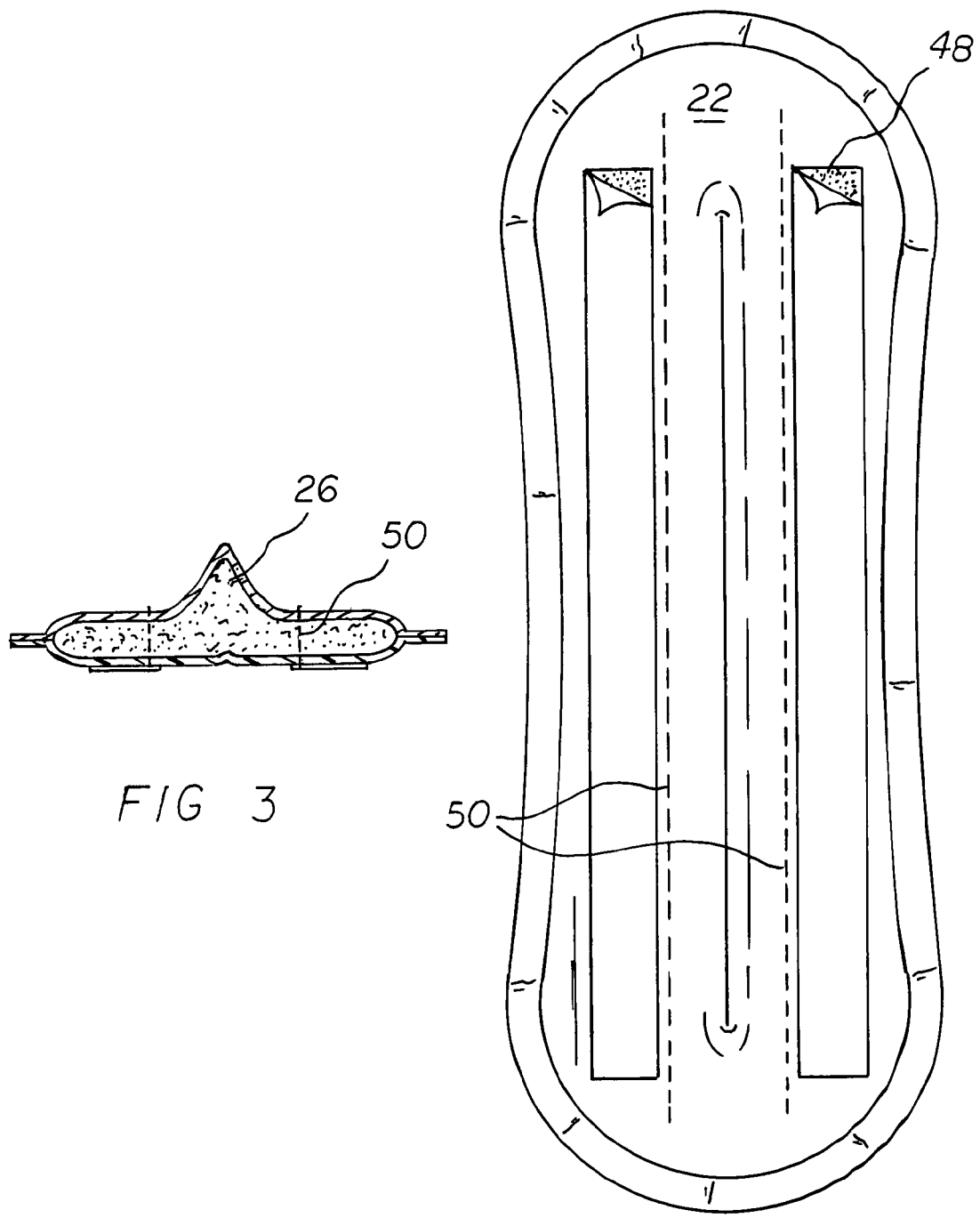
FIG. 3 is a cross sectional view taken along line 3-3 of FIG. 1.
FIG. 4 is a bottom view of the panty liner/pad taken along line 4-4 of FIG. 2.

With reference now to the drawings, and in particular to FIG. 1 thereof, the preferred embodiment of the new and improved panty liner/pad system embodying the principles and concepts of the present invention and generally designated by the reference numeral 10 will be described.

The present invention, the panty liner/pad system 10 is comprised of a plurality of components. Such components in their broadest context include a body portion and a vertically oriented projection. Such components are individually configured and correlated with respect to each other so as to attain the desired objective.

First provided is a body portion 14. The body portion has opposed semicircular ends 16. The ends are spaced centrally by a length of between 6.25 and 7.0 inches. The body portion has opposed concave sides 18. The concave sides are spaced centrally by a maximum width of between 2.15 and 2.35 inches when measured at the midpoint of the length. The concave sides are spaced by a minimum width of between 2.4 and 2.6 inches when measured adjacent to the ends. The body portion has a longitudinal axis. In this manner the body portion is divided into two symmetrically shaped lateral halves. The body portion has a latitudinal axis. In this manner the body portion is divided into two symmetrically shaped longitudinal halves. The body portion prior to use has a planar upper surface 20. The body portion prior to use also has a planar lower surface 22. The upper and lower planar surfaces are spaced by a thickness of between 0.5 and 1.0 inch over the majority of their extents.

A vertically oriented projection 26 is provided. The projection extends upwardly from the upper surface of the body portion. The projection is integrally formed with the body portion. The body portion has a lower edge. The lower edge is centrally positioned on the longitudinal axis of the body portion. The lower edge has a length of between 4.0 and 5.0 inches. The projection has an upper edge. The upper edge is centrally positioned above the longitudinal axis of the body portion. The upper edge has a length of between 0.7 and 0.8 inches. The projection has a forward end 28. The forward end is in a generally triangular configuration. The projection has a rearward end 30. The rearward end is in a generally triangular configuration. The forward and rearward ends each have a concave edge 32, 34. The concave edge is provided between the upper and lower edges of the projection. The forward end and the projection there adjacent have a thickness between 25 and 50 percent greater than the thickness of the rearward end and projection there adjacent. The body portion and the projection are adapted to curve with the user's vagina and are held in place by the user's labia majora during use.

Further provided is a sheet 38 of a moisture impervious material. The sheet has a periphery 40. The periphery has stitching 42. In this manner the sheet is attached to the lower surface of the body portion adjacent to the periphery. The sheet is fabricated of a moisture impervious material. The body portion and the projection are fabricated of a moisture absorbing material.

Provided next is a pair of adhesive strips 48. The strips are coupled to the lower surface of the body portion. The strips are positioned parallel with and laterally spaced from the longitudinal centerline. The strips are adapted to removably couple the body portion to panties of the user concurrently with the projection being held by the labia majora of the user.

Provided last are two parallel lines of stitching 50 through the body portion on opposite sides of the projection. This helps the system maintain its proper shape.

Figures 5, 6:
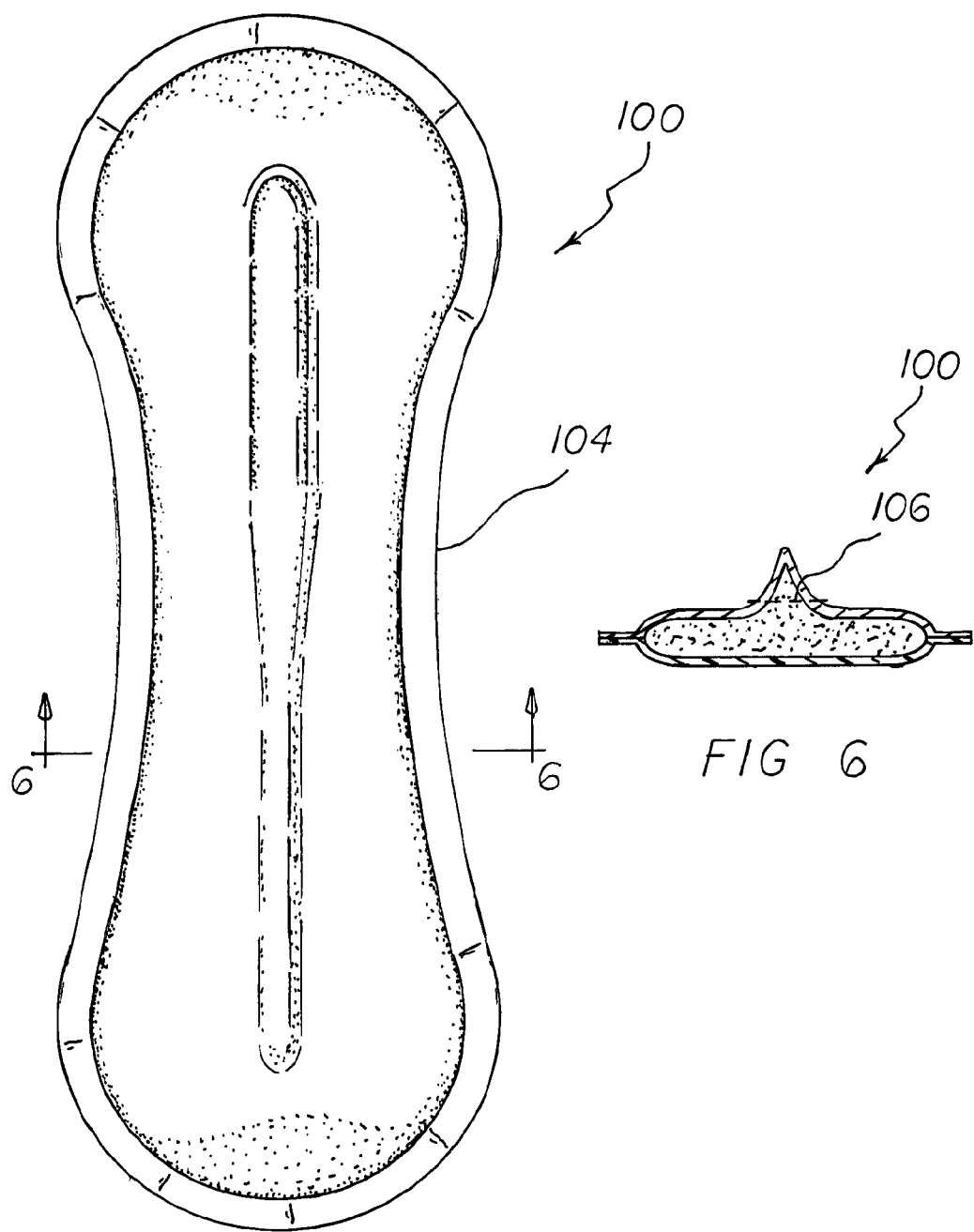
FIG. 5 is a plan view similar to FIG. 1 but illustrating an alternate embodiment of the invention.
FIG. 6 is a cross sectional view taken along line 6-6 of FIG. 5.

An alternate embodiment 100 of the present invention is provided. A width 104 is provided at the center of the body portion. The width is less than 90 percent of the width of the body portion elsewhere. Further included is one line of stitching 106 through the projection adjacent to the body portion. This helps the system maintain its shape during use. Note FIGS. 5 and 6.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A panty liner/pad system for securing panty liners and menstrual pads in a proper absorbing position through an interlabial projection, the system comprising, in combination:

a body portion having opposed semicircular ends spaced centrally by a length of between 6.25 and 7.0 inches, the body portion having opposed concave sides spaced centrally by a maximum width of between 2.15 and 2.35 inches when measured at the midpoint of the length and the concave sides being spaced by a minimum width of between 2.4 and 2.6 inches when measured adjacent to the ends, the body portion having a longitudinal axis dividing the body portion into two symmetrically shaped lateral halves, the body portion having a latitudinal axis dividing the body portion into two symmetrically shaped longitudinal halves, the body portion prior to use having a planar upper surface and a planar lower surface, the upper and lower planar surfaces spaced by a thickness of between 0.5 and 1.0 inch over the majority of their extents;

a vertically oriented projection extending upwardly from the upper surface of the body portion, the projection being integrally formed with the body portion, the body portion having a lower edge centrally positioned on the longitudinal axis of the body portion, the lower edge having a length of between 4.0 and 5.0 inches, the projection having a linear upper edge centrally positioned above the longitudinal axis of the body portion, the upper edge having a height of between 0.7 and 0.8 inches along its entire length, the projection having a forward end in a generally triangular configuration, the projection having a rearward end in a generally triangular configuration, the forward and rearward ends of the projection being equally spaced from the respective ends of the body portion, the forward and rearward ends each having a concave edge between the upper and lower edges of the projection, the forward end and the projection there adjacent having a thickness between 25 and 50 percent greater than the thickness of the rearward end and projection there adjacent, the body portion and the projection adapted to curve with the user's vagina and to be held in place by the user's labia majora during use;

a sheet of a moisture impervious material, the sheet having a periphery with stitching attaching the sheet to the lower surface of the body portion adjacent to the periphery, the sheet being fabricated of a moisture impervious material, the body portion and the projection being fabricated of a moisture absorbing material; and a pair of adhesive strips coupled to the lower surface of the body portion, the strips positioned parallel with and laterally spaced from the longitudinal centerline, the adhesive strips adapted to removably couple the body portion to panties of the user concurrently with the projection being held by the labia majora of the user, the body portion and the projection adapted to curve with the user's vagina and to be held in place by the user's labia majora during use.

* * * * *